(12) United States Patent
Hoftman

(10) Patent No.: US 8,752,987 B1
(45) Date of Patent: Jun. 17, 2014

(54) VACUUM SECURED LIGHTWEIGHT SURGICAL LIGHT HANDLE COVER

(76) Inventor: Moshe Mike Hoftman, Calabasas, CA (US)

( * ) Notice: Subject to any disclaimer, the term of this patent is extended or adjusted under 35 U.S.C. 154(b) by 443 days.

(21) Appl. No.: 12/984,814

(22) Filed: Jan. 5, 2011

(51) Int. Cl.
  *F21V 21/08* (2006.01)
(52) U.S. Cl.
  USPC .......................................... 362/400; 362/399
(58) Field of Classification Search
  USPC .................................................. 362/399–400
  See application file for complete search history.

(56) References Cited

U.S. PATENT DOCUMENTS

| | | | | |
|---|---|---|---|---|
| 5,709,465 A | * | 1/1998 | Lanzone | 362/400 |
| 6,447,149 B1 | * | 9/2002 | Kaforey et al. | 362/400 |

* cited by examiner

*Primary Examiner* — William Carter

(57) ABSTRACT

The present invention solves the problem of secure engagement of a thin gauge light handle cover to a light handle. This is possible by way of a simple addition to existing light handle covers. Vacuum structures are a critical improvement of the present invention over the prior art. The prior art has uniformly tried to use a seal between the shield rim and the light handle cover behind which a vacuum would be attempted to be formed. Where the post and shield covering sections have sufficient structural strength, such a seal and vacuum can be obtained. With thin gauge polymers, it is simply not practical.

8 Claims, 5 Drawing Sheets

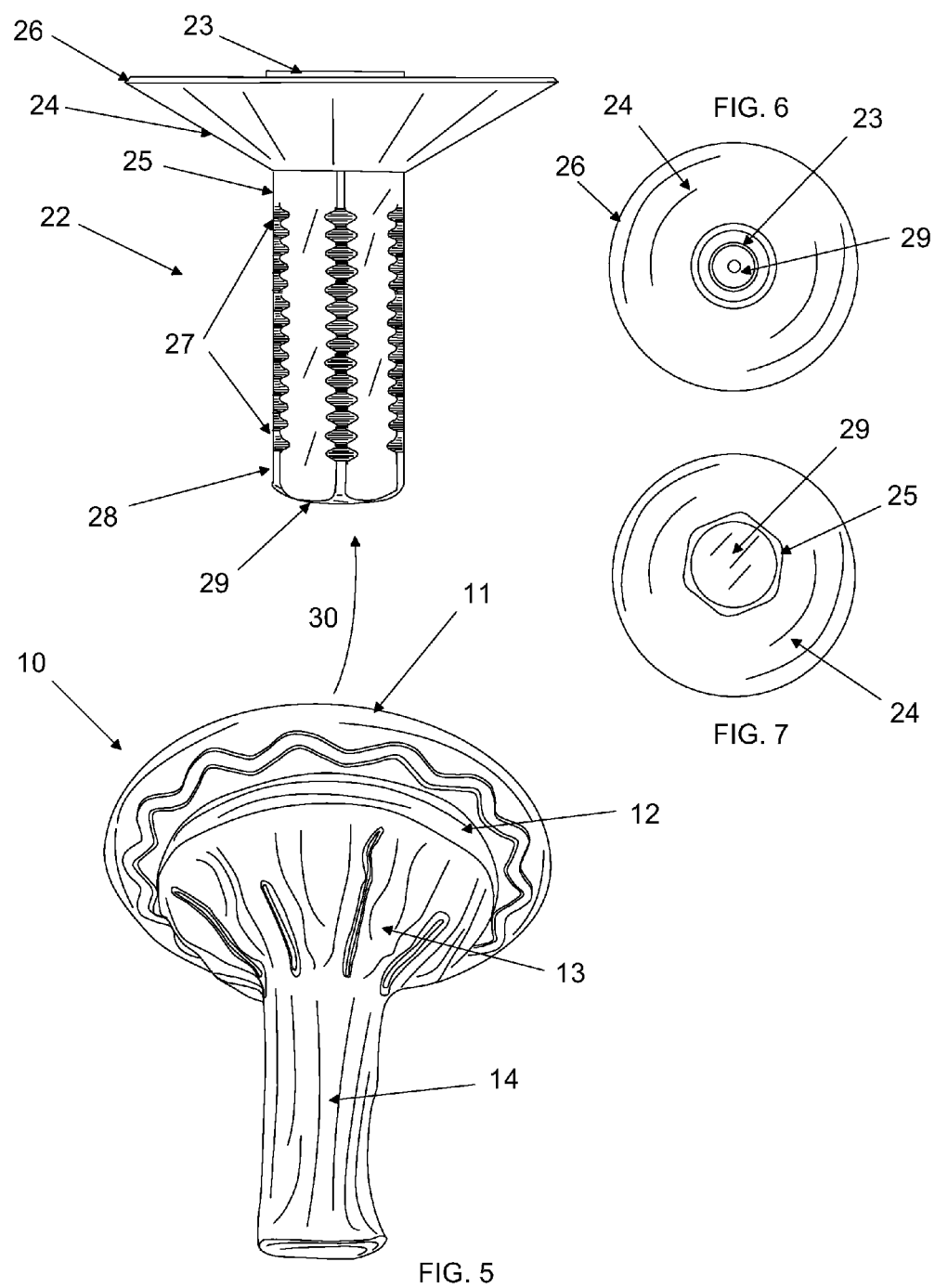

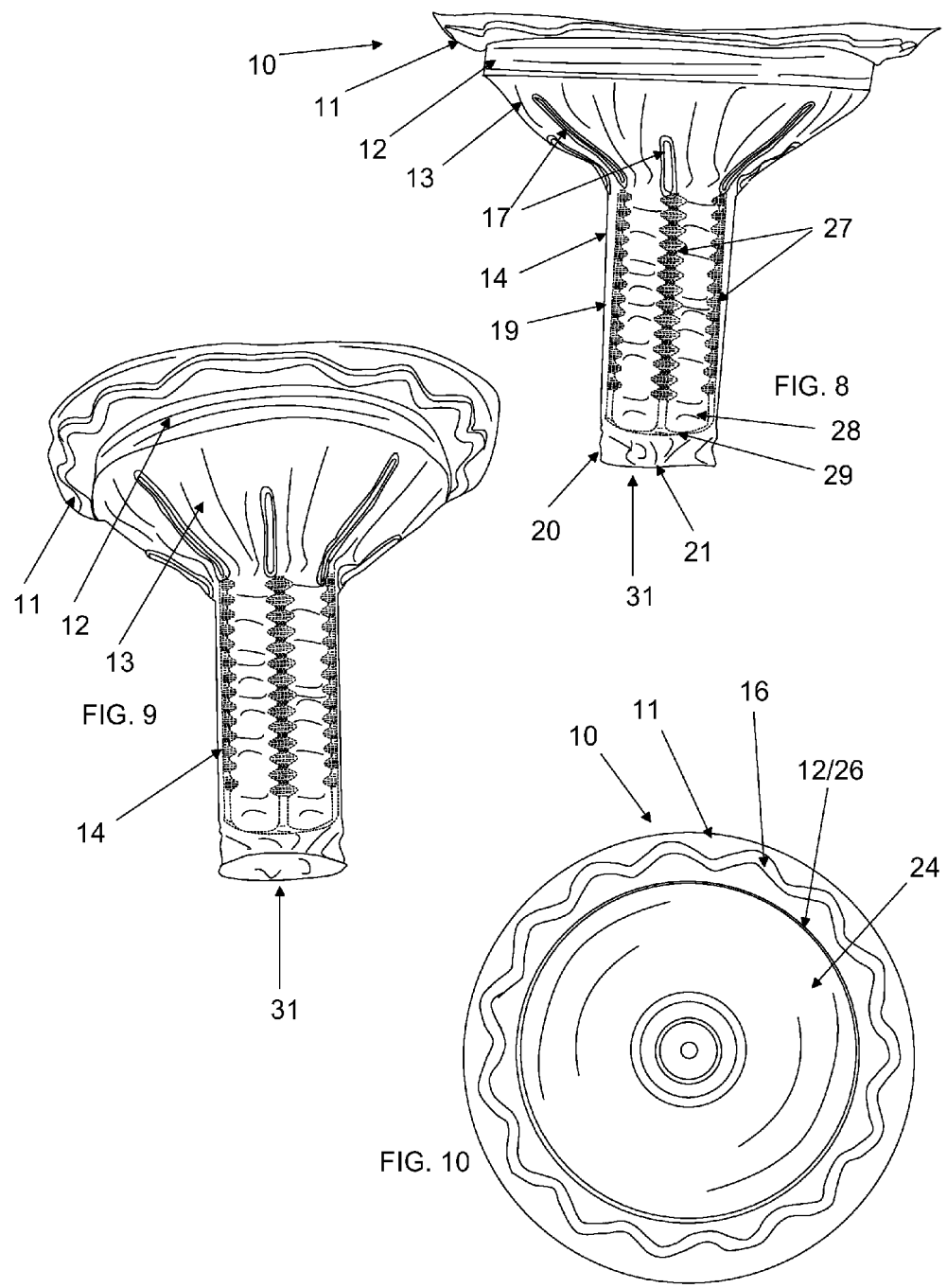

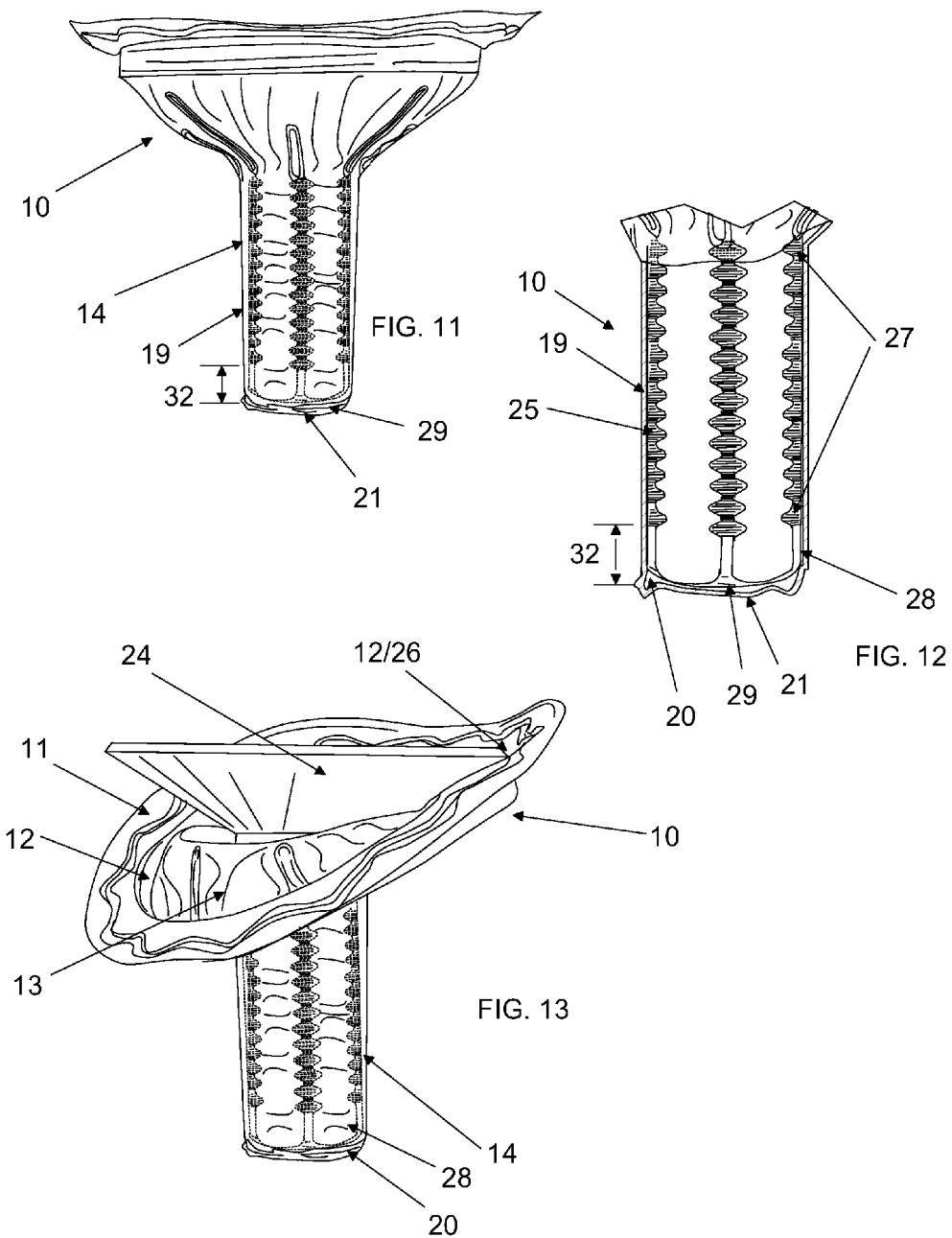

VACUUM SECURED LIGHTWEIGHT SURGICAL LIGHT HANDLE COVER

FIELD OF THE INVENTION

The present invention relates to sterile light handle covers required during surgical procedures for grasping a handle extension of a surgery light without contaminating the user's gloved hand. More specifically, the present invention relates to a particular type of surgical light handle cover where essentially the entire cover is formed from a single lightweight and flexible polymer so that the entire cover can be compressed for flattened storage.

BACKGROUND OF THE INVENTION

The present invention relates in general to hospital surgery room equipment and specifically to a disposable cover for the handle of a surgical room light fixture which is normally positioned above the operating table and handled by the surgeon and or nurse during operations. In operating rooms and surgical surroundings, special and unique lighting is employed due to the unique requirements for both high-powered lighting and the attainment of a sterile environment. This lighting commonly consists of an arrangement of lights suspended from above the operating area so as to project and focus the rays upon the surgical area. Due to the use of such lighting, surgical personnel find it necessary to adjust the angle of incidence upon the operating areas or to bring the light closer to the area which is being operated on during surgery. To accomplish this task, the moveable lighting fixture usually has a handle situated in the middle of the light housing and depends therefrom. To aid in the pursuit of cleanliness and in order to aid in the creation of a more sterile environment, the handle of the lighting housing must be sterile because of the constant contact with the hands of surgical personnel who are attempting to adjust the lighting. The handle must not become contaminated and render the environment not sterile.

It is well known that every facet of medical care is reviewed repeatedly to determine if either cost or space for medical supplies can be reduced. However, a conflict regularly arises between personnel responsible for saving cost and space and those who are responsible for delivery of excellent medical care. Those responsible for saving cost look for ways to use less expensive products. Those responsible for delivery of health care resist using what they often rightly perceive to be lower quality products being either urged or forced upon them by procurement departments. During the era of the light handle covers of U.S. Pat. Nos. 4,605,124, 5,599,093, and 5,156,456 (naming as inventor the present inventor and disclosing a type of collapsible light handle cover), costs were not so intensely scrutinized. The relatively large amount of polymer used for such light handle covers allows for a wide range of styles and structures due to the structural strength endowed by thicker cover walls.

As an example of how the drive for cost savings has challenged prior art designs, U.S. Pat. No. 6,447,149 and a product currently sold by Cory Bros. (Shenley, Hertferdshire, United Kingdom), under Ref. CB3611 as an Operating Room Light Handle Cover (hereafter referred to as the Cory Product, which was designed by the present inventor), have attempted to use an overall structure of the light handle cover to so as to engage a conical shield part of the light handle and thereby form a vacuum securitization of the light handle cover to the light handle.

It has become apparent that at some point (at approximately a light handle cover thickness of about 4 thousandths of an inch or less), it is structurally impossible for such light handle covers to maintain adequate vacuum engagement to the light handle. Such lightweight, thin gauge light handle covers meet the requirements of being low cost and collapsible for storage. However, if they are made of reduced internal diameter to elastically and frictionally remain attached to the light handle, they are necessarily somewhat difficult to apply to the light handle. This is a substantial drawback where a user in a sterile glove must try to install the light handle cover, condom-like, first onto the post part of the light handle and then, without being allowed to grasp the wide outer rim edges of the light handle cover, to push structurally collapsible conical protector walls into full peripheral sealing contact with the outer rim of the conical protector of the light handle. Such manipulation and difficulty necessarily causes vibration and unnecessary movement of the surgical lamp structure as well as makes it much more likely a user may inadequately engage a light handle cover to the light handle, resulting in the light handle cover falling off the light handle during surgery.

There is a need for a light handle cover using lightweight, lower gauge polymer which will assure retention of a light handle cover on the light handle during surgery while providing a low cost and completely collapsible structure.

SUMMARY OF THE INVENTION

The present invention comprises a disposable cover for the handle of the surgical room light fixture, which is normally positioned above the operating table and handled by the surgeon and or nurse during operations, the cover comprising a sterile, disposable thin walled impervious polymer having localized vacuum sealing means. Much of the general shape of a light handle cover is pre-determined by standard sizes and shapes of light handles used in surgical procedures. A currently popular light handle has a post part with hexagonal 1.5 inch thick cross section and a length of about 3 inches, with a frustro-conical shield extending by about one inch up from a top of the handle, expanding to about 4 inches across at the widest part of the cone. A flexible light handle cover must provide a liquid and pathogen impervious barrier between a user's gloved hand and the outside surface of the post part and the shield that allows a user to use the post part to direct the surgical lamp beams. These requirements are well known in the art and impose on every flexible light handle cover a general shape conforming to the outside surfaces of the post part and the shield.

Further and in compliance with the requirements of all flexible light handle covers, a preferred form of the invention incorporates many features of the Cory Product as described above. That product comprises, from a top of the light handle downward, a reinforced top rim, a shield rim engagement section, a ribbed section, and a post section. The present inventor, in the course of development of that product, noticed that ever more elastically tighter engagement was required between the light handle cover's post section and the light handle's post part as well as the light handle cover's shield rim engagement section and the light handle's shield rim as the thickness of the light handle cover's polymer was reduced. The present inventor noticed that application and removal of the light handle cover resulted in substantial difficulty for the users and thereafter set out to find a solution to this problem.

The present invention solves the problem of secure engagement of a thin gauge light handle cover to a light handle. This is possible by way of a simple addition to existing light handle covers. Vacuum means have been described above as a critical improvement of the present invention over the prior art. The prior art has uniformly tried to use a seal between the shield rim and the light handle cover behind which a vacuum would be attempted to be formed. Where the post and shield covering sections have sufficient structural strength, such a seal and vacuum can be obtained. With thin gauge polymers, it is simply not practical.

Vacuum means in the present invention permit loose fit between a top portion of the post part of the light handle and the invention light handle cover with relatively tighter fit farther down. The post part of the light handle often comprises notches or grooves to improve a user's grip. However, at the free end of the post part there is a smooth circumference zone where the invention light handle cover provides a relatively tight fit. The post covering section of the invention light handle cover extends farther down beyond the free end of the post part, forming a vacuum section. Having easily slipped the invention light handle cover into a position covering the post part and engaging the shield rim will find an effectively gas tight zone seal at the smooth circumference zone with the invention light handle cover. A user presses upward on the vacuum section of the light handle cover, thereby expelling air contained therein past the zone seal and to atmosphere, resulting the vacuum zone being compressed against the free end of the post part under secure vacuum pressure.

Vacuum means of the present invention provides frictional and vacuum fixing of the lower end of the light handle cover to the post part of the light handle. With such dual fixing of the light handle cover to the light handle, the present inventor has found that even inadvertent pulling of the shield covering section away from the light handle shield cannot dislodge the invention light handle cover from the light handle. Moving the vacuum engaged portion of the light handle cover to a small but essential area of the light handle cover results in secure fixation of thin gauge light handle covers without excessive and deleterious elastic tension over the structure of the light handle cover.

It is an object of the invention to reduce to a small area a vacuum fixing of a thin walled light handle cover to a surgical light handle.

It is a further object of the invention to reduce elastic tension required to maintain a thin walled light handle cover on a light handle It is a further object of the invention to extend the length of a post part covering section of a thin walled light handle cover past a free end of the light handle, thereby forming a pocket of air which may be expelled by upward outside compression to form a vacuum pocket at the free end of the light handle.

It is yet a further object of the invention to improve fixing of thin walled light handle covers to light handles.

BRIEF DESCRIPTION OF THE DRAWINGS

FIG. 5 is the light handle cover of FIG. 1 oriented in a manner to be applied to a surgical light handle, whose top and bottom views are shown respectively in FIGS. 6 and 7.

FIGS. 8, 9 and 10 are respectively side, bottom perspective, and top views of the light handle cover of FIG. 5 as applied to the light handle of that same figure with a vacuum zone extended.

FIGS. 11 and 12 are respectively side and light handle cover cutaway views of the light handle cover of FIG. 5 as applied to the light handle of that same figure with a vacuum zone compressed.

FIG. 13 is the light handle cover and light handle of FIG. 11 with a shield covering part of the light handle cover pulled down to show that a vacuum in the vacuum zone is maintained after such action.

DETAILED DESCRIPTION OF THE INVENTION

The invention is now discussed with reference to the figures.

Figure 1:
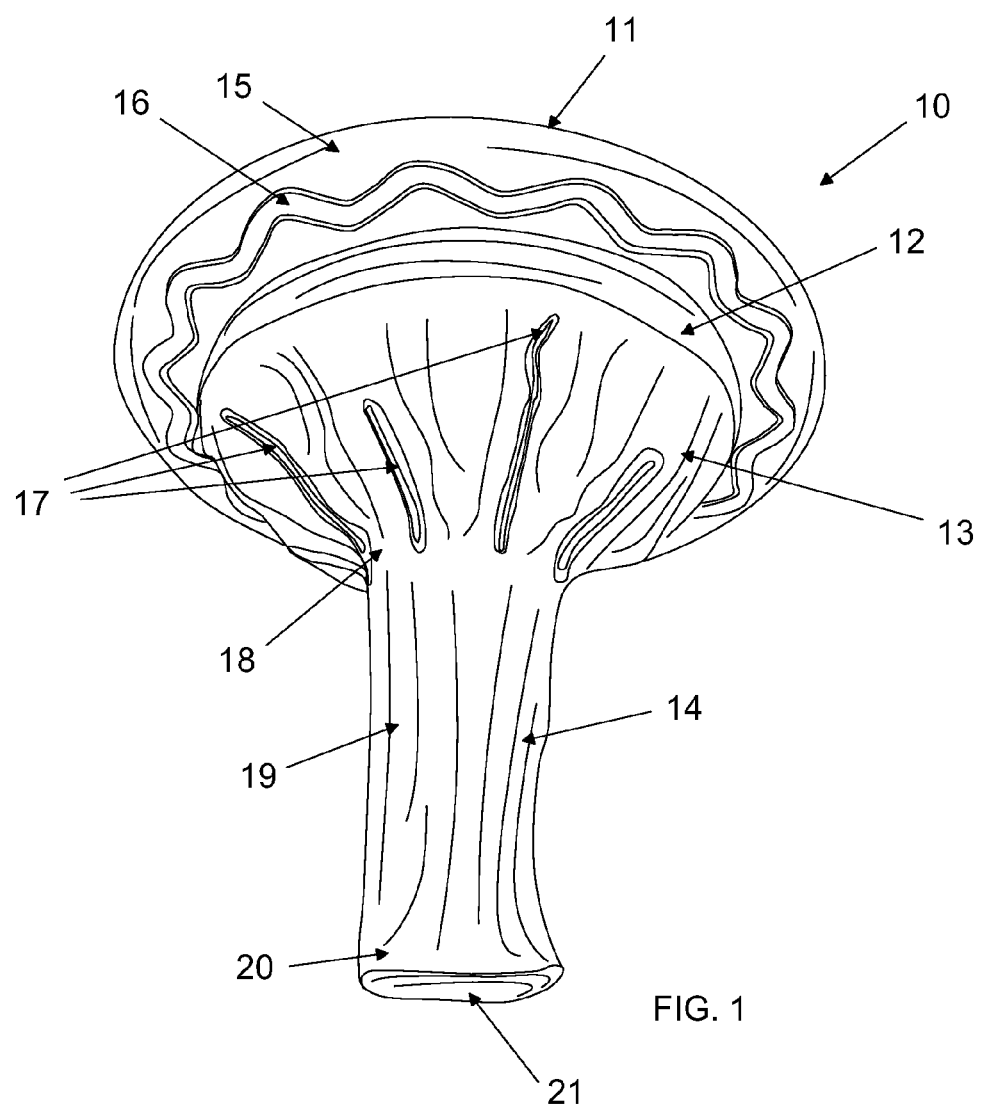
FIG. 1 is a bottom perspective view of a preferred form of the invention light handle cover in the Cory Product style.

FIG. 1 is a bottom perspective view of a preferred form of the invention light handle cover 10 in the Cory Product style, comprising a top rim section 11, from which extends cylindrically downward a shield rim engagement section 12. A ribbed conical section 13 extends down and inward from a lower edge of section 12. A generally flexible and cylindrical post covering section 14 extends downward from a lower edge of the ribbed conical section 13, which section 14 is sealed at a bottom end with base sheet 21.

Cover 10 is in one form of the invention comprised of a polymer with a generally uniform thickness of from 1 to 10 mils, or more preferably, from 1.5 to 2.5 mils. Cover Cover 10 is in another form of the invention comprised of a polymer with a thickness of from 1.5 to 2.5 mils in section 14 and the other sections of greater thickness. Section 14 having a reduced thickness compared with sections 11 to 13 allows for greater elastic tension for covering of the post part of the light handle with minimal effort in sliding section 14 onto it, as the greater rigidity and structural strength of sections 11 to 13 allow the user to push upward against those sections to draw section 12 onto the post part of the light handle cover.

Polymers which may be used for the invention light handle cover include low density polyethylene, high density polyethylene, polypropylene, polystyrene, polycarbonate, polytetrafluoroethylene, tetrafluoroethylene and fluorinated ethylene propylene.

Cover 10 comprises top rim section 11 having an upwardly concave continuous wave rib 16 which preserves radial structural strength of section 11 so that it stays extended beyond a rim edge of a shield of a light handle when the light handle cover is applied. Section 12 is generally a short cylindrical section accomplishing the function described in the '149 patent for the interaction between section 24 of the light handle cover and rim 50 of the light handle, which is to provide a generally inadequate but mainly elastic contact seal between the atmosphere and the environment between the light handle cover and the light handle. Section 13 provides the majority of a cover for a frustro-conical section of the surgical light handle, having multiple and upward concave longitudinal ribs 17 about the conical surface of section 13.

Post covering section 14 comprises a post covering part 19 and a vacuum part 20 below it.

Figure 2:
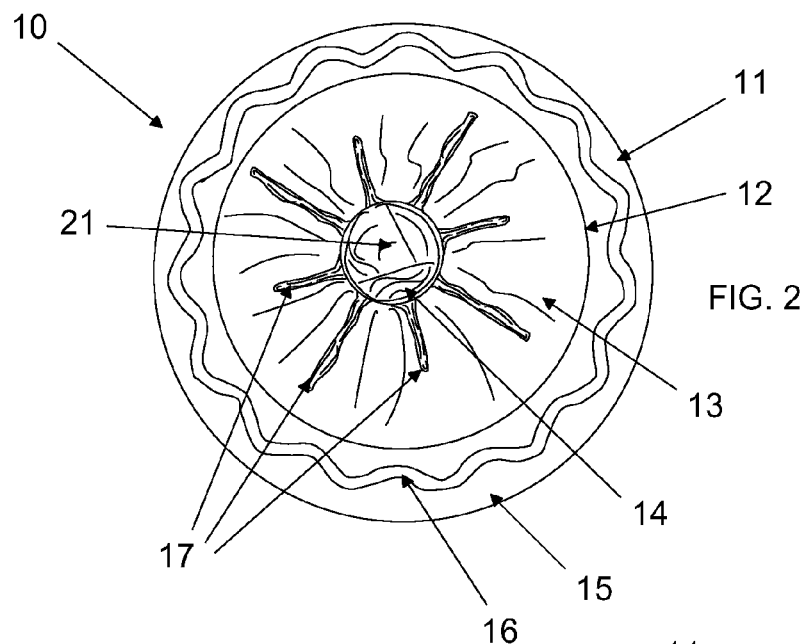
FIGS. 2 and 3 are respectively top and bottom views of the light handle cover of FIG. 1.
Figure 3:
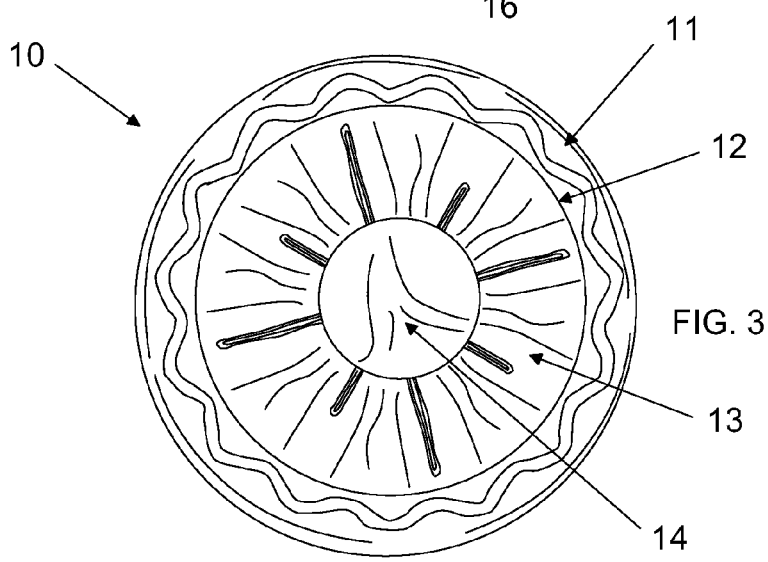
Figure 4:
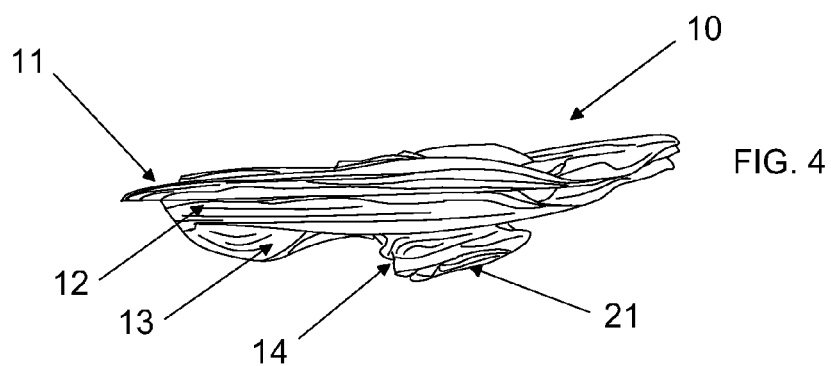
FIG. 4 is a side view of a compressed state of the light handle cover of FIG. 1.

FIGS. 2 and 3 are respectively top and bottom views of the light handle cover 10 of FIG. 1. FIG. 4 is a side view of a compressed state of the light handle cover 10 of FIG. 1, where a compressed height of the cover 10 is about 0.5 inches to about 1.0 inch. The extreme flexibility of the invention thin walled light handle cover essentially eliminates special folding or orientation to obtain the compressed state of FIG. 4. Simple top to bottom direction compression results in the compressed state of cover 10 of FIG. 4.

FIG. 5 is the light handle cover 10 of FIG. 1 oriented in a manner to be applied to a surgical light handle 22, whose top and bottom views are shown respectively in FIGS. 6 and 7, wherein a shield 24 comprises a shield rim 26 and the post part 25 comprises a hexagonal horizontal cross section with edge grooves 27 located above smooth circumference zone 28 and terminating in post end 29. A threaded receiver 23 allows for the light handle 22 to be screwed to a threaded extension of a surgical lamp. Referring again to FIG. 5, cover 10 is moved upward in direction 30 to be applied to light handle 22.

FIGS. 8, 9 and 10 are respectively side, bottom perspective, and top views of the light handle cover 10 of FIG. 5 as applied to the light handle of that same figure with a vacuum zone 20 in extended state. Zone 20 contains a pocket of air sealed against the atmosphere by way of elastic tension of a lower part of post covering part 19 about zone 28. To create a vacuum in vacuum zone 20, a user presses up in direction 31 toward end 29.

FIGS. 11 and 12 are respectively side and light handle cover cutaway views of the light handle cover 10 of FIG. 5 as applied to the light handle of that same figure with a vacuum zone 20 compressed. Seal zone 32 is shown having a lower area of part 19 stretched sealingly about an ungrooved part of post part 25, where side walls of vacuum zone 20 are compressed down by their polymeric memory, thereby maintaining vacuum in the vacuum zone 20.

FIG. 13 is the light handle cover 10 and light handle 22 of FIG. 11 with a shield covering part of the light handle cover (sections 11 to 13) pulled down to show that a vacuum in the vacuum zone 20 is maintained after such action. In the prior art, vacuum seal would be instantly lost upon such action, where in the invention light handle cover, vacuum fixing of the light handle cover 10 is maintained due to a smaller but effective vacuum zone 20 being sealed against atmosphere at zone 28.

Zone 28 is preferably an unbroken and smooth circumferential band of greater than 0.25 inches to 3 inches or more. Zone 28 may be located along the downward length of post part 22 of the light handle, whereby it need not be located at the free end of post part 22, but that is its preferred location. Further, the air pocket described in the vacuum zone 20 preferred to be greater than or equal to 2 cubic centimeters, more preferably greater than or equal to 5 cubic centimeters.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. A combination of a surgical light handle and a light handle cover comprising:
    (a) the light handle adapted to be connected with a surgical lamp and having a post part extending down from cone shaped shield, where the post part comprises a smooth circumference zone;
    (b) the light handle cover comprising an upper shield cover and a lower post cover, where the upper shield cover is generally conical and adapted to closely cover an outside surface of the shield and the lower post cover is adapted to closely cover the post part;
    (c) the lower post cover comprising an elastic seal which is adapted to elastically seal the smooth circumference zone against atmosphere when the light handle cover is engaged to the light handle;
    (d) the lower post cover comprising a vacuum zone extending the lower post cover beyond a free end of the post part when the light handle cover is engaged to the light handle;
    (e) the light handle cover is formed entirely of flexible, thin walled polymer from 1 to 10 mils thick and is adapted to be reduced in overall height from a state generally in the form of the light handle into a flattened, compressed state for storage due to a flexibility and foldability of the flexible, thin walled polymer; and
    (f) the thickness of the thin walled polymer is from 1.5 to 2.5 mils and the thickness of the upper shield cover is greater than that of the lower post cover.

2. The combination of claim 1 wherein the upper shield section comprises a topmost rim section which extends outward from a rim of the shield when the light handle cover is engaged to the light handle.

3. The combination of claim 2 wherein the upper shield section further comprises a vertical cylindrical rim contact section which extends downward from the rim section and adapted to generally engage the rim of the shield when the light handle cover is engaged to the light handle.

4. The combination of claim 3 wherein the upper shield section further comprises a conical ribbed section which extends downward and inward from the rim contact section and adapted to generally engage the shield when the light handle cover is engaged to the light handle.

5. The combination of claim 1 wherein the smooth circumference zone is adjacent to the free end of the post part.

6. The combination of claim 5 wherein an upper zone of the lower post cover is not substantially elastically engaged to the post part when the light handle cover is engaged to the light handle.

7. The combination of claim 5 wherein an upper zone of the lower post cover is not elastically engaged to the post part when the light handle cover is engaged to the light handle but a lower zone of the lower post cover is so elastically engaged.

8. A combination of a surgical light handle and a light handle cover comprising:
    (a) the light handle adapted to be connected with a surgical lamp and having a post part extending down from cone shaped shield, where the post part comprises a smooth circumference zone;
    (b) the light handle cover comprising an upper shield cover and a lower post cover, where the upper shield cover is generally conical and adapted to closely cover an outside surface of the shield and the lower post cover is adapted to closely cover the post part;
    (c) the lower post cover comprising an elastic seal which is adapted to elastically seal the smooth circumference zone against atmosphere when the light handle cover is engaged to the light handle;
    (d) the lower post cover comprising a vacuum zone extending the lower post cover beyond a free end of the post part when the light handle cover is engaged to the light handle;
    (e) light handle cover is formed entirely of thin walled polymer from 1 to 10 mils thick; and
    (f) the thickness of the thin walled polymer of the lower post cover is from 1.5 to 2.5 mils and the thickness of the upper shield cover is greater than that of the lower post cover.

* * * * *